United States Patent [19]

Hassler et al.

[11] Patent Number: 4,834,106
[45] Date of Patent: May 30, 1989

[54] LITHOTRIPTER WITH LOCATING SYSTEM INTEGRATED THEREWITH AND METHOD FOR ITS USE

[75] Inventors: Dietrich Hassler, Uttenreuth; Erhard Schmidt, Erlangen, both of Fed. Rep. of Germany

[73] Assignee: Siemens Aktiengesellschaft, Berlin and Munich, Fed. Rep. of Germany

[21] Appl. No.: 151,154

[22] Filed: Feb. 1, 1988

[30] Foreign Application Priority Data

Feb. 4, 1987 [DE] Fed. Rep. of Germany ....... 3703334

[51] Int. Cl.$^4$ .......................... A61B 8/00; A61B 17/22
[52] U.S. Cl. .............................. 128/660.03; 128/24 A; 128/328
[58] Field of Search ..................... 128/328, 24 A, 660, 128/660.03

[56] References Cited

U.S. PATENT DOCUMENTS

| | | | |
|---|---|---|---|
| 3,716,826 | 2/1973 | Green . | |
| 4,526,168 | 7/1985 | Hassler et al. | 128/24 A |
| 4,620,545 | 11/1986 | Shene et al. | 128/328 |
| 4,669,483 | 6/1987 | Hepp et al. | 128/660 |

FOREIGN PATENT DOCUMENTS 3328039 2/1985 Fed. Rep. of Germany .

Primary Examiner—Ruth S. Smith
Attorney, Agent, or Firm—Hill, Van Santen, Steadman & Simpson

[57] ABSTRACT

A lithotripter for disintegrating a calculus in the body of a patient has a shock wave source which emits shock wave pulses which are focussed to the calculus by an acoustic lens. As seen in the propagation direction of the shock wave pulses, a semi-transmissive acoustic mirror is disposed in front of the acoustic lens at a fixed angle. An ultrasound transducer, which is part of an ultrasound locating system, such as an ultrasound sector scanner, is disposed laterally with respect to the acoustic mirror, so that ultrasound waves are transmitted by the transducer to the calculus, and the reflected waves are transmitted from the calculus to the transducer, reflected by the acoustic mirror. Shock wave pulses from the shock wave source are only minimally impeded by the mirror, so that the therapy is substantially uninfluenced by the presence of the mirror. The ultrasound signals are used to identify the position of the calculus in the patient, so that the position can be continuously observed, even during the time in which the shock pulses are acting on the calculus. The approach path of the shock wave pulse to the calculus can also be ultrasonically monitored.

13 Claims, 1 Drawing Sheet

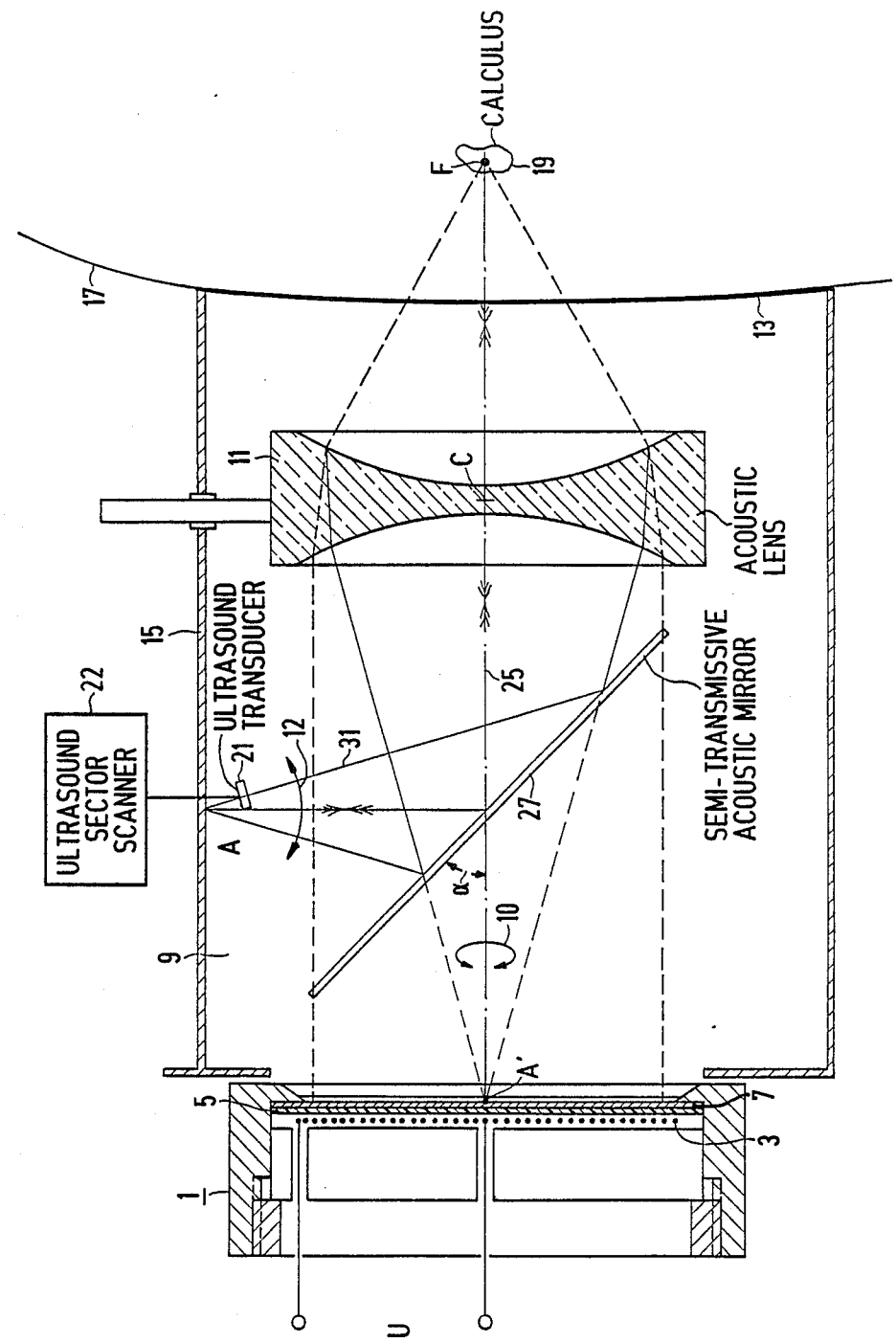

LITHOTRIPTER WITH LOCATING SYSTEM INTEGRATED THEREWITH AND METHOD FOR ITS USE

BACKGROUND OF THE INVENTION

1. Field of the Invention

The present invention relates to lithotripsy devices, and in particular to such devices combined with a means for locating the calculus to be disintegrated in the body of a patient.

2. Description of the Prior Art

A shock wave device for disintegrating a calculus in the human body is generally described, for example, in German OS No. 33 28 039. A shock wave tube is used as the shock wave source. The shock wave tube has an electrical coil, an insulating foil, and a copper membrane arranged in sequence. When a current pulse is applied to the coil, eddy currents are generated in the membrane, causing the membrane to be rapidly repelled from the coil. A shock wave is formed in the adjacent transmission medium, such as water. The shock wave is focussed by an acoustic lens having a focal point disposed in the calculus of the patient after a suitable positioning procedure. The calculus may be, for example, a kidney stone.

Locating the position of the calculus in the body of the patient is of great significance to the degree of therapeutic success, as well as for decreasing the load on the patient during therapy. The chances for successful therapy increase, and the load on the patient decrease, as the targeting becomes more precise. It is known to undertake such locating using x-ray devices. A disadvantage of such conventional locating means, however, is that the position of the calculus cannot be monitored during the complete shock wave treatment, because this would result in an undesireable x-radiation load on the patient. X-ray images are therefore recorded only from time to time during therapy to monitor the position of the calculus.

For continuously monitoring the calculus position, it is known to use an ultrasound system as the locating means. For example, German Patent No. 34 27 001 corresponding to U.S. Pat. No. 4,669,483 discloses a locating and positioning method wherein the calculus is located with an ultrasound oscillator, prescribed identification marks are set, and the calculus and the focal point of the shock wave system are subsequently mechanically brought into coincidence.

It is also known from German OS No. 31 19 295 corresponding to U.S. Pat. No. 4,526,168 to undertake locating of the calculus using the shock wave sour In the system described therein, the shock wave source is an arrangement of a plurality of piezo-electric transducer elements. This method, however, can be used only given shock wave sources wherein the shock wave pulse is produced using such piezo-electric elements.

SUMMARY OF THE INVENTION

It is an object of the present invention to provide a lithotripter having an ultrasound locating means integrated therewith for continuously monitoring the position of the calculus, the ultrasound locating means being integrable with the lithotripter regardless of the type of shock wave source used.

It is another object of the present invention to provide such a lithotripter which permits the calculus position to be monitored during the action of the shock wave pulses thereon.

The above objects are achieved in accordance with the principles of the present invention in a lithotripter having a semi-transmissive acoustic mirror disposed between the shock wave source and the focussing means. An ultrasound transducer, which is part of an ultrasound sector scanner, is disposed in the lithotripter laterally of the acoustic mirror. The shock waves pass sufficiently unimpeded through the acoustic mirror so that calculus disintegration still is accomplished, but a sufficient portion of the ultrasound waves transmitted and received between the transducer and the calculus are reflected by the mirror to still permit locating and observation of the calculus.

The mirror is preferably planar. It is possible, however, to employ a mirror with a suitable curvature, which can be selected to achieve a particular scan format.

The shock wave pulse passing through the acoustic mirror is attenuated only slightly. Reflections arise at both boundary surfaces (front and back sides). The acoustic mirror is therefore relatively thin, because the superimposition of the two reflections generate two images shifted relative to each other in the propagation direction. This shift will be decreased as the mirror is made thinner. The loss of energy due to reflection and attenuation at the acoustic mirror for both the shock waves and the locating pulses can be compensated by using a slightly higher transmission energy.

The respective degrees of sound energy which are transmitted and reflected by the acoustic mirror can be set by selection of the characteristic acoustic impedence of the mirror. The attenuation of the shock wave pulse in the mirror can be compensated by using a pulse having a higher initial amplitude than would otherwise be used. The shock wave otherwise assumes an unimpeded course through the acoustic mirror. The ultrasound locating signal generated by the ultrasound transducer is laterally reflected by the acoustic mirror and directed toward the calculus. The ultrasound signals reflected by the calculus are in turn laterally reflected by the acoustic mirror toward the ultrasound transducer. The reflected echos are thus received by the transducer, and analyzed by the processing circuitry in the ultrasound sector scanner. Continuous observation of the position of the calculus is thus possible, even during the action of the shock wave pulse on the calculus.

DESCRIPTION OF THE DRAWINGS

The single FIGURE is a side sectional view of a lithotripter with an ultrasound locating means integrated therewith constructed in accordance with the principles of the present invention.

DESCRIPTION OF THE PREFERRED EMBODIMENTS

A lithotripter is shown in the drawing constructed in accordance with the principles of the present invention, and having a shock wave source generally referenced at 1. The shock wave source 1 includes a flat electrical coil 3 having a metallic membrane 7 (consisting of, for example, copper) disposed in front thereof, and separated from the coil 3 by an insulating foil 5. The coil 3 may be charged with a voltage pulse U. An approach path 9 follows the membrane 7. An acoustic lens 11, functioning as a focussing means for the shock wave pulses, is disposed in the approach path 9. The approach path 9 is terminated at the side closest to the patient by a coupling membrane 13. A housing is formed by a cylindrical tube 15, closed at one end by the shock wave source 1 and at the other end by the coupling membrane 13. The interior is filled with a coupling fluid, such as water.

The coupling membrane 13 is positioned against the skin of a patient 17. The shock wave source 1 is positioned so that the focus F of the acoustic lens 11 is coincident with the position of a calculus 19, for example, a kidney stone.

As seen in the shock wave propagation direction, a semitransmissive planar acoustic mirror 27 is disposed in front of the acoustic lens 11. The acoustic mirror 27 is preferably disposed at an angle α relative to the central axis 25 of the lens 11, the angle α preferably being 45°. The acoustic mirror 27 is rigidly placed preferably approximately half way between the shock wave source 1 and the acoustic lens 11.

An ultrasound transducer 21, which is part of a mechanical ultrasound sector scanner 22, is mounted to the interior of the tube 15 laterally opposite the acoustic mirror 27. The ultrasound transducer 21 is rotatable, as schematically indicated by the double curved arrow 12, around an axis which is perpendicular to the plane of the drawing and which proceeds through point A. The point A may lie roughly on the wall of the tube 15. Fan-shaped ultrasound locating signals 31 emanating from the ultrasound transducer 21 and emitted in succession are reflected in the direction toward the acoustic lens 11 by the acoustic mirror 27. The lens 11 reshapes these signals into a converging sector scan. The image generating system of the scanner 22 is adapted to the converging sector scan and, in contrast to conventional sector scans, does not make use of a divergent scan.

The ultrasound transducer 21 and the acoustic mirror 27 are preferably rotatable in combination around the central axis 25, as schematically indicated by the circular arrow 10, so that an examination region shaped like a truncated cone can be observed in the patient 17.

The acoustic mirror 27 is as thin as possible so that multiple reflections from the mirror 27 are as small as possible. The thickness is preferably less than 0.5 mm. The acoustic mirror 27 may consist of plastic, such as plexiglass. The position of the acoustic mirror 27 between the shock wave source 1 and the acoustic lens 11 is preferably selected so that the apparent origin A' of the ultrasound locating signals 31 lies on the emission surface of the shock wave source 1, i.e., on the membrane 7.

The convergent sector scan of the patient 17 is achieved by a suitable selection of the distance of the acoustic mirror 27 between the membrane 7 of the shock wave source 1 and the acoustic lens 11.

At least one advantage of the lithotripter described above is that the calculus 19 can be observed during the entire treatment. This includes the time during which the shock wave pulse acts on the calculus 19. Moreover, the approach path of the shock wave pulse can also be observed in the entire volume of the lithotripter, and can be suitably selected.

A synchronization unit (not shown) may additionally be provided, which triggers a shock wave pulse when the echo of the ultrasound signal is received by the transducer 21. At such a point in time, the ultrasound system is "looking" precisely at the calculus 19.

Although modifications and changes may be suggested by those skilled in the art it is the intention of the inventors to embody within the patent warranted hereon all changes and modifications as reasonably and properly come within the scope of their contribution to the art.

We claim as our invention:

1. A lithotripter for disintegrating a calculus disposed in the body of a patient comprising:
   means for generating shock wave pulses;
   means for focussing said shock wave pulses to said calculus;
   a semi-transmissive acoustic mirror disposed between said means for generating shock wave pulses and said means for focussing, said semi-transmissive mirror permitting shock wave pulses to pass therethrough sufficient to disintegrate said calculus; and
   an ultrasound locating means for identifying the position of said calculus in said body, said ultrasound locating means including an ultrasound transducer disposed laterally of said semi-transmissive acoustic mirror to transmit and receive ultrasound signals to and from said calculus reflected by said semi-transmissive acoustic mirror, said semi-transmissive mirror reflecting said ultrasound signals sufficient to observe said calculus.

2. A lithotripter as claimed in claim 1, wherein said focussing means has a central axis, and further comprising means for rotating said mirror and said ultrasound transducer in combination around said central axis.

3. A lithotripter as claimed in claim 1, wherein said means for focussing has a central axis, and wherein said acoustic mirror is disposed at an angle of substantially 45° relative to said central axis.

4. A lithotripter as claimed in claim 1, wherein said mirror has a thickness of less than 0.5 mm.

5. A lithotripter as claimed in claim 1, wherein said mirror consists of plastic.

6. A lithotripter as claimed in claim 1, wherein said ultrasound transducer generates an ultrasound locating beam having an apparent origin, and wherein said means for generating shock wave pulses has an emission surface, and wherein said acoustic mirror is disposed a distance from said means for generating shock wave pulses such that said apparent origin of said ultrasound locating beam lies on said emission surface.

7. A lithotripter as claimed in claim 1, wherein said means for generating shock wave pulses has an emission surface, and further comprising means for moving said ultrasound transducer to undertake a sector scan of a portion of said patient, and wherein the distance between said emission surface and said means for focussing is selected such that the ultrasound signals emitted by said ultrasound transducer during said sector scan movement converge behind said means for focussing, as seen in the direction of shock wave pulse propagation.

8. A lithotripter as claimed in claim 1 further comprising means for mechanically moving said ultrasound transducer to undertake a sector scan of a portion of said patient.

9. A lithotripter as claimed in claim 1, wherein said acoustic mirror is planar.

10. A lithotripter as claimed in claim 1, wherein said ultrasound locating means is an ultrasound sector scanner.

11. A method for operating a lithotripter to disintegrate a calculus disposed in the body of a patient while continuously monitoring the position of said calculus in said patient, said method comprising the steps of:
- generating shock wave pulses;
- passing said shock wave pulses substantially unimpeded through a semi-transmissive acoustic mirror sufficient to disintegrate said calculus;
- focussing said shock waves after passing through said acoustic mirror to a point coincident with said calculus;
- generating an ultrasound locating beam in said lithotripter from a position within said lithotripter disposed laterally of said acoustic mirror;
- reflecting said ultrasound locating beam by said acoustic mirror in the direction of said calculus, and reflecting ultrasound echo signals from said calculus by said mirror to said position disposed laterally of said mirror in said lithotripter sufficient to observe said calculus; and
- processing the ultrasound echo signals to observe said calculus in said patient.

12. A method as claimed in claim 11 wherein said lithotripter has a central axis, and wherein said acoustic mirror is disposed at an angle relative to said central axis, and wherein said lithotripter has an ultrasound transducer for generating and receiving said ultrasound locating and echo signals, and comprising the additional steps of rotating said mirror and said transducer in combination around said central axis.

13. A lithotripter as claimed in claim 11, wherein said lithotripter includes an ultrasound transducer for transmitting said ultrasound locating beam and receiving said ultrasound echos, and comprising the additional step of moving said ultrasound transducer relative to said mirror to undertake a sector scan of a portion of said patient.

* * * * *